: US 8,316,721 B2
(45) Date of Patent: Nov. 27, 2012

(12) United States Patent
Hong et al.

(54) APPARATUS AND METHOD FOR NON-DESTRUCTIVE MEASUREMENT OF BENDING STIFFNESS OF GDL FOR FUEL CELL (75) Inventors: Bo Ki Hong, Seoul (KR); Kook Il Han, Seoul (KR); Ji Yeon Park, Gyeonggi-do (KR); Byeong Heon Jeong, Gyeonggi-do (KR); Sang Yeoul Ahn, Seoul (KR)

(73) Assignee: Hyundai Motor Company, Seoul (KR)

( * ) Notice: Subject to any disclaimer, the term of this patent is extended or adjusted under 35 U.S.C. 154(b) by 282 days.

(21) Appl. No.: 12/911,478

(22) Filed: Oct. 25, 2010

(65) Prior Publication Data
US 2011/0314928 A1 Dec. 29, 2011

(30) Foreign Application Priority Data
Jun. 29, 2010 (KR) .................. 10-2010-0061685

(51) Int. Cl.
*G01N 3/20* (2006.01)

(52) U.S. Cl. ......................................................... 73/849
(58) Field of Classification Search ..................... 73/849
See application file for complete search history.

(56) References Cited

U.S. PATENT DOCUMENTS

| 6,007,933 | A | * | 12/1999 | Jones | 429/481 |
| 7,632,589 | B2 | * | 12/2009 | Kawashima et al. | 429/481 |
| 8,250,929 | B2 | * | 8/2012 | Lin et al. | 73/818 |
| 2011/0136044 | A1 | * | 6/2011 | Han et al. | 429/518 |

FOREIGN PATENT DOCUMENTS

| JP | 2005108674 A | 4/2005 |
| KR | 10-0911589 | 6/2009 |

* cited by examiner

*Primary Examiner* — Lisa Caputo
*Assistant Examiner* — Octavia Davis-Hollington
(74) *Attorney, Agent, or Firm* — Edwards Wildman Palmer LLP; Peter F. Corless (57) ABSTRACT

The present invention provides an apparatus and method for non-destructive measurement of bending stiffness of a gas diffusion layer (GDL) for a fuel cell by measuring a sagging length of a GDL sample, which can be used for a fuel cell, without damaging or destroying the GDL sample.

14 Claims, 6 Drawing Sheets

FIG. 1

[Prior Art]

FIG. 2a

[Prior Art]

-GDL samples for measurement of bending stiffness-

FIG. 2b

[Prior Art]

FIG. 3

(a) - GDL raw material sheet -

(b) - GDL samples for measurement of sagging length -

| GDL types | Examples of measurement of sagging length |
|---|---|
| GDL1-F |  |
| GDL4-P |  |
| GDL5-P |  |

FIG. 8

APPARATUS AND METHOD FOR NON-DESTRUCTIVE MEASUREMENT OF BENDING STIFFNESS OF GDL FOR FUEL CELL

CROSS-REFERENCE TO RELATED APPLICATION

This application claims under 35 U.S.C. §119(a) the benefit of Korean Patent Application No. 10-2010-0061685 filed Jun. 29, 2010, the entire contents of which are incorporated herein by reference.

BACKGROUND (a) Technical Field

The present disclosure relates, in general, to an apparatus and method for the non-destructive measurement of bending stiffness of a gas diffusion layer (GDL) for a fuel cell. More particularly, it relates to an apparatus and method for non-destructively and indirectly measuring the bending stiffness of a GDL for a fuel cell by measuring a sagging length of a GDL sample, which can be used for a fuel cell, without damaging or destroying the GDL sample.

(b) Background Art

In general, a polymer electrolyte membrane fuel cell (PEMFC) is used as a fuel cell for a vehicle. The PEMFC should be able to stably operate over a wide current density range and is typically composed of a fuel cell stack configured by stacking several hundreds of unit cells so that it can exhibit a high-power performance of at least several tens of kW under various operational conditions of the vehicle [S. Park, J. Lee, and B. N. Popov, J. Power Sources, 177, 457 (2008)].

The fuel cell generates electricity through an electrochemical reaction between hydrogen and oxygen in a polymer electrolyte membrane-electrode assembly. Hydrogen supplied to an anode as an oxidation electrode of the fuel cell is dissociated into hydrogen ions and electrons. The hydrogen ions are transmitted to a cathode as a reduction electrode through a polymer electrolyte membrane, and the electrons are transmitted to the cathode through an external circuit. At the cathode, the hydrogen ions and electrons react with oxygen containing air to generate electricity and heat and, at the same time, produce water as a reaction by-product.

When an appropriate amount of water produced during the electrochemical reaction is present in the fuel cell, it performs the function of maintaining the humidity of a membrane electrode assembly (MEA). However, when an excessive amount of water is present and is not appropriately removed, a flooding phenomenon occurs at high current density, and the flooding water prevents the reactant gases from being efficiently supplied to the fuel cell, which results in an increase in voltage loss.

Therefore, in order to improve the productivity of the fuel cells stacks for fuel cell vehicles and stabilize their quality, it is necessary to efficiently assemble and test the parts of the fuel cell stacks and, at the same time, to rapidly and accurately measure the properties of the parts of the fuel cell stacks.

There remains a need in the art for apparatus and method for non-destructive measurement of bending stiffness of a gas diffusion layer (GDL) for a fuel cell, that can be used without damaging or destroying the GDL sample.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides an apparatus and method for non-destructive measurement of bending stiffness of a gas diffusion layer (GDL) for a fuel cell by measuring a sagging length of a GDL sample, which can be preferably used for a fuel cell, without damaging or destroying the GDL sample. The apparatus and methods of the present invention are different from a conventional method for measuring the bending stiffness of a GDL sample obtained by cutting a GDL raw material sheet. Accordingly, the GDL sample used in the measurement is not damaged, and thus it can be recycled in the assembly of a fuel cell stack. Moreover, as the GDL sample prepared for the manufacturing of the fuel cell stack is used as it is for the measurement, it takes only about 30 seconds to select a GDL sample and measure the sagging length of the GDL sample, and thus it is possible to suitably reduce the inspection time about 40 to 120 times compared to the conventional method. As a result, it is possible to indirectly evaluate the bending stiffness of all the gas diffusion layers, not a part of the GDL raw material sheet for the manufacturing of the fuel cell stack, and thus it is possible to considerably improve the manufacturing efficiency of the fuel cell stack.

In one aspect, the present invention provides an apparatus for non-destructive measurement of bending stiffness of a gas diffusion layer for a fuel cell, the apparatus preferably including first and second columns erected vertically on a support means having a predetermined area; a sagging length measuring means integrally attached to the first column along the longitudinal direction to measure a sagging length of a gas diffusion layer sample; a sagging length limit value sensor suitably mounted on the sagging length measuring means to determine whether the measured sagging length reaches a limit value; and a gas diffusion layer sample holder suitably mounted at the top of the second column to accommodate one end of the gas diffusion layer sample having a size equal to that of a gas diffusion layer raw material sheet.

In a preferred embodiment, the sagging length limit value sensor may further include a contact-sensitive electronic sensor installed on the top surface thereof.

In another preferred embodiment, the gas diffusion layer sample holder may include a sample support mounted at the top of the second column; a pair of fixing plates integrally mounted at the top of the sample support; and a moving plate suitably mounted on the inner side of each of the fixing plates to be moved up and down and fixed by a position fixing pin in a desired position, wherein the space between the top surface of a horizontal plate of each fixing plate and the bottom surface of a horizontal plate of each moving plate may form an insertion hole into which the gas diffusion layer sample is inserted and supported.

In still another preferred embodiment, the gas diffusion layer sample holder may include a single-type fixing plate having an open top and open front and rear sides; and a cover slidably connected to a vertical plate of the fixing plate to be moved up and down, wherein the space between the top surface of a horizontal plate of the fixing plate and the bottom surface of the cover may form an insertion hole into which the gas diffusion layer sample is inserted and supported.

In yet another preferred embodiment, the height of the insertion hole may be 1 to 5% greater than the thickness of the gas diffusion layer sample, and the width of the insertion hole may be 1 to 5% greater than the width of the gas diffusion layer sample.

In still yet another preferred embodiment, the gas diffusion layer sample holder may be suitably formed of a transparent material to allow a user to observe damage or deformation of the gas diffusion layer sample with the naked eye during measurement of the sagging length of the gas diffusion layer sample.

In a further preferred embodiment, the sagging length measuring means may include a sagging length measuring ruler having marked gradations to allow a user to determine the sagging length of the gas diffusion layer sample with the naked eye or a laser optical sensor for calculating a sagging length of the gas diffusion layer sample by detecting the lengths of the gas diffusion layer sample before and after sagging.

In one aspect, the present invention provides a method for non-destructive measurement of bending stiffness of a gas diffusion layer for a fuel cell, the method including: pre-measuring bending stiffness of various types of gas diffusion layers, which are to be actually assembled into a fuel cell stack; inserting one end of each of the gas diffusion layers into a gas diffusion layer sample holder in a non-contact manner, measuring the length that the other end of each of the gas diffusion layers sags, and obtaining an average value and standard deviation from the measured sagging lengths; comparing the pre-measured bending stiffness of the gas diffusion layer with the sagging length of the gas diffusion layer obtained in a non-contact manner to establish a correlation between the bending stiffness and the sagging length and, and the same time, defining the sagging length, which is correlated with the bending stiffness, as a sagging length limit value to determine a normal product; and measuring the sagging length of a new gas diffusion layer and comparing the measured sagging length with the sagging length limit value to determine the new gas diffusion layer as a normal product if the sagging length of the new gas diffusion layer is within the sagging length limit value or to determine the new gas diffusion layer as an abnormal product if the sagging length of the new gas diffusion layer exceeds the sagging length limit value.

In a preferred embodiment, the method may further include reusing the gas diffusion layer, which is determined as a normal product, by supplying the gas diffusion layer to an actual assembly line of a fuel cell stack.

Other aspects and preferred embodiments of the invention are discussed infra.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The above and other features of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

Reference numerals set forth in the Drawings includes reference to the following elements as further discussed below:

| | |
|---|---|
| 10: lower plate support | 11: first column |
| 12: second column | 20: sagging length measuring means |
| 30: sagging length limit value sensor | 32: contact-sensitive electronic sensor |
| 40: GDL sample holder | 41: sample support |
| 42: fixing plate | 42a: horizontal plate |
| 42b: vertical plate | 43: position fixing pin |
| 44: moving plate | 44a: horizontal plate |
| 44b: vertical plate | 45: insertion hole |
| 46: fixing plate | 46a: horizontal plate |
| 46b: vertical plate | 47: cover |
| 48: insertion hole | 50: GDL sample |

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Various test apparatuses and methods have been proposed to rapidly and accurately measure the properties of the parts of fuel cell stacks, and may be classified as follows: (1) those which relate to the fuel cell stack assembling/quality test/ activation such as an automatic assembling apparatus of fuel cell stacks, which is disclosed in Korean Patent Publication No. 10-2009-0106217, devices and methods for testing airtightness of fuel cell stacks, which are disclosed in Korean Patent Publication No. 10-2009-0113429 and Korean Patent Publication No. 10-2009-0108478, and an activation method of fuel cell, which is disclosed in Korean Patent Publication No. 10-2007-0060760; (2) those which relate to the evaluation of properties of parts such as a method for evaluating the spatial distribution of an ionomer in a fuel cell membrane-electrode assembly, which is disclosed in U.S. Patent Publication No. US2009/0189076A1 by Michael P. Balogh & Frederick A. Hayes, a device and method for measuring a pin hole of a polymer electrolyte membrane, which is disclosed in Korean Patent Publication No. 10-2009-0107610, an automated system for manufacturing parts of a fuel cell stack, which is disclosed in Korean Patent Publication No. 10-2009-0111898, and a device for testing airtightness of a fuel cell separator, which is disclosed in Korean Patent Publication No. 10-2009-0113432; and (3) those which relate to the measurement of performance of fuel cells such as a method and apparatus for measurement of fuel cell high frequency resistance in the presence of large undesirable signals, which is disclosed in U.S. Publication No. US2008/0091367A1 by David Rea, Kenneth L. Kaye, Robert S. Foley, Michael F. Zawisa, and Clark G. Hochgraf, and a method for maximum net power calculation for a fuel cell system based on online polarization curve estimation, which is disclosed in U.S. Publication No. US2009/0197125A1 by John P. Salvador, Sriram Ganapathy, Kiran Mallavarapu, Frank X. Leo, and Balasubramanian Lakshmanan.

With the progress of research and development and mass-production of PEMFCs for vehicles, extensive research and development of methods for evaluating the properties of a gas diffusion layer (GDL) and the microstructure/performance mechanisms of the GDL, which plays an important role in ensuring stable performance of the fuel cell stack among its various parts, has recently been performed.

Techniques related to the evaluation of the properties of the gas diffusion layer include, for example, an integrated multi-measurement system which can measure the thickness, electric resistance, and differential pressure of gas diffusion layer for a polymer electrolyte fuel cell with respect to compression, which is disclosed in Korean Patent No. 10-0902316, and a method for sensing separation of a gas diffusion layer of a membrane electrode assembly, which is disclosed in Korean Patent Publication No. 10-2009-0108767.

Such a gas diffusion layer is generally composed of a microporous layer and a macroporous substrate.

The gas diffusion layer is attached to the outer surface of each of catalyst layers coated for an oxidation electrode and a reduction electrode on both sides of a polymer electrolyte membrane of a fuel cell. The gas diffusion layers function to supply reactant gases such as hydrogen and air (oxygen), transmit electrons produced by an electrochemical reaction, and discharge water produced by the reaction to minimize the flooding phenomenon in the fuel cell.

At present, commercially available gas diffusion layers have a dual layer structure including a microporous layer (MPL) having a pore size of less than 1 μm when measured by mercury intrusion and a macroporous substrate (or backing) having a pore size of 1 to 300 μm [L. Cindrella, A. M. Kannan, J. F. Lin, K. Saminathan, Y. Ho, C. W. Lin, J. Wertz, J. Power Sources, 194, 146 (2009); X. L. Wang, H. M. Zhang, J. L. Zhang, H. F. Xu, Z. Q. Tian, J. Chen, H. X. Zhong, Y. M. Liang, B. L. Yi, Electrochim. Acta, 51, 4909 (2006)].

The microporous layer of the gas diffusion layer is suitably formed by mixing carbon powder such as carbon black, acetylene black carbon, and black pearl carbon with polytetrafluoroethylene (PTFE) hydrophobic agent and coating the mixture on one or both sides of the macroporous substrate.

The macroporous substrate of the gas diffusion layer is generally composed of carbon fiber and hydrophobic agents such as polytetrafluoroethylene and fluorinated ethylene propylene (FEP) [C. Lim and C. Y. Wang, Electrochim. Acta, 49, 4149 (2004)], and may be formed of carbon fiber cloth, carbon fiber felt, and carbon fiber paper [S. Escribano, J. Blachot, J. Etheve, A. Morin, R. Mosdale, J. Power Sources, 156, 8 (2006); M. F. Mathias, J. Roth, J. Fleming, and W. Lehnert, Handbook of Fuel Cells-Fundamentals, Technology and Applications, Vol. 3, Ch. 42, John Wiley & Sons (2003)].

It is necessary to optimize the structural design of the gas diffusion layer for the fuel cell vehicle such that it provides appropriate performance according to the application fields and operational conditions. In general, in the manufacturing of the gas diffusion layer for the fuel cell vehicle, the carbon fiber felt or carbon fiber paper is preferred to the carbon fiber cloth since the carbon fiber felt and carbon fiber paper have excellent properties such as reactant gas supply properties, product water discharge properties, compression properties, and handling properties.

Moreover, the gas diffusion layer has a significant effect on the performance of the fuel cell according to complex and various structural differences such as the thickness, gas permeability, compressibility, hydrophobicity of microporous and macroporous layers, structure of carbon fiber, porosity/pore size distribution, pore tortuosity, electrical resistance, and bending stiffness.

Furthermore, the gas diffusion layer should have an appropriate level of stiffness to provide excellent performance in the fuel cell and to provide excellent handling properties when several hundreds of cells are assembled in the fuel cell stack.

Figure 1:
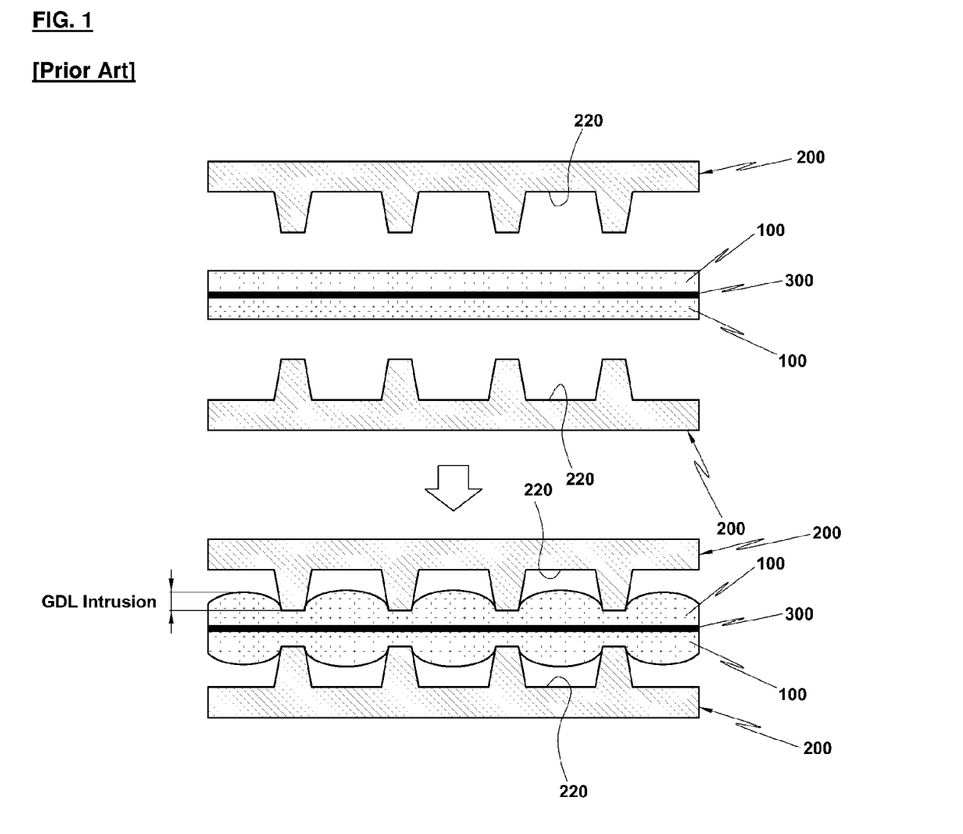
FIG. 1 is a schematic diagram illustrating that conventional gas diffusion layers intrude into flow field channels of a bipolar plate.

According to the previous reports, when the stiffness of the gas diffusion layer is insufficient in the fuel cell, as shown in FIG. 1, the gas diffusion layers 100 stacked on both surfaces of a polymer electrolyte membrane-electrode assembly 300 may intrude into flow field channels 220 of a bipolar plate 200 (or separator) during assembly of the fuel cell (which is called "GDL intrusion") [Iwao Nitta, Tero Hottinen, Olli Himanen, Mikko Mikkola, J. Power Sources, 171, 26 (2007); Yeh-Hung Lai, Pinkhas A. Rapaport, Chunxin Ji, Vinod Kumar, J. Power Sources, 184, 120 (2008); J. Kleemann, F. Finsterwalder, W. Tillmetz, J. Power Sources, 190, 92 (2009); M. F. Mathias, J. Roth, M. K. Budinski, U.S. Pat. No. 7,455,928 B2; T. Kawashima, T. Osumi, M. Teranishi, T. Sukawa, US 2008/0113243 A1].

When the GDL intrusion into the flow field channels of the bipolar plate occurs, the channel space required for transferring reactant gases and product water is reduced, and the contact resistance between the gas diffusion layer, the ribs or lands of the bipolar plate, and the polymer electrolyte membrane electrode assembly is increased, which causes a significant deterioration in the fuel cell performance.

Therefore, it is important to increase the mechanical properties such as bending stiffness of the gas diffusion layer and use gas diffusion layers having high bending stiffness during manufacturing of the fuel cell stacks.

In particular, in order to facilitate the manufacturing of the fuel cell stacks for vehicles and ensure their stable quality, it is necessary to rapidly and easily evaluate the bending stiffness of several hundreds of gas diffusion layers used at a time in the fuel cell stack.

During the evaluation of the bending stiffness of the gas diffusion layers, if the sample is evaluated as normal, it is important to recycle the corresponding sample, thereby increasing the recycling rate.

Conventionally, the bending stiffness of the gas diffusion layers is measured by various methods such as a 2-point bending test (DIN 53121), a 3-point bending test (ASTM D790), or a taber-type tester (ASTM D5342).

Figure 2A:
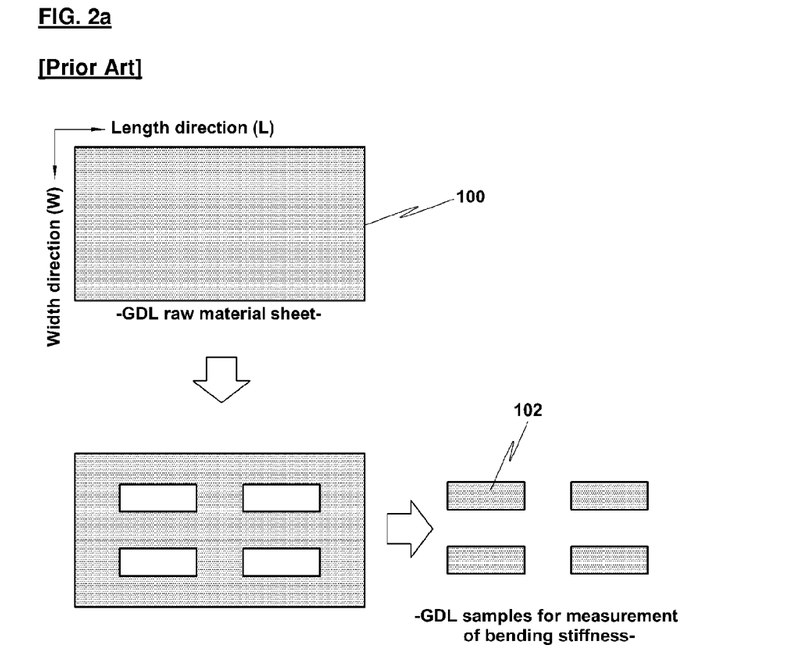
FIG. 2A is a schematic diagram illustrating a conventional process of preparing samples by cutting a GDL raw material sheet to measure bending stiffness of gas diffusion layers.
Figure 2B:
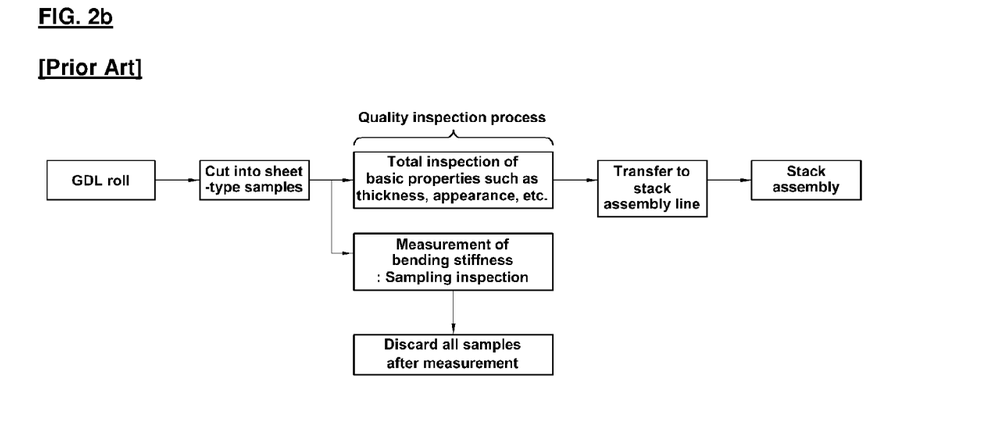
FIG. 2B is a process diagram illustrating a conventional process of inputting a GDL raw material sheet to a process of manufacturing a fuel cell stack.

However, as shown in FIGS. 2A and 2B, the conventional measurement methods have the following drawbacks: as a GDL raw material sheet 100 is cut into samples 102 having a smaller size, the shape of the GDL raw material sheet 100 is destroyed; and as the bending stiffness is measured using the cut samples 102, the GDL raw material sheet 100 used for the measurement cannot be reused.

Moreover, it takes a relatively long time (about 20 minutes to 1 hour) to cut the GDL raw material sheet into samples, investigate the basic properties of the samples such as thickness, appearance, etc., measure the bending stiffness, and discard the GDL raw material sheet and the samples after the measurement. Further, as the samples are obtained by locally cutting the GDL raw material sheet, the samples cannot represent the bending stiffness of all the gas diffusion layers used in the manufacturing of the fuel cell stacks for vehicles.

As described herein, in preferred aspects the present invention features an apparatus for non-destructive measurement of bending stiffness of a gas diffusion layer for a fuel cell, the apparatus comprising a first column and a second column, wherein the first and second columns are erected on a support means, a sagging length measuring means to measure a sagging length of a gas diffusion layer sample, a sagging length limit value sensor to determine whether the measured sagging length reaches a limit value, and a gas diffusion layer sample holder.

In one embodiment, the first and second columns are erected vertically on a support means having a predetermined area.

In another embodiment, the sagging length measuring means is integrally attached to the first column along the longitudinal direction to measure a sagging length of a gas diffusion layer sample.

In another further embodiment, the sagging length limit value sensor is mounted on the sagging length measuring means to determine whether the measured sagging length reaches a limit value.

In still another embodiment, the gas diffusion layer sample holder is mounted at the top of the second column to accommodate one end of the gas diffusion layer sample having a size equal to that of a gas diffusion layer raw material sheet.

In another aspect, the present invention features a method for non-destructive measurement of bending stiffness of a gas diffusion layer for a fuel cell, the method comprising pre-measuring bending stiffness of various types of gas diffusion layers, which are to be actually assembled into a fuel cell stack, inserting one end of each of the gas diffusion layers into a gas diffusion layer sample holder in a non-contact manner, measuring the length that the other end of each of the gas diffusion layers sags, and obtaining an average value and standard deviation from the measured sagging lengths, comparing the pre-measured bending stiffness of the gas diffusion layer with the sagging length of the gas diffusion layer obtained in a non-contact manner to establish a correlation between the bending stiffness and the sagging length and, and the same time, defining the sagging length, which is correlated with the bending stiffness, as a sagging length limit value to determine a normal product; and measuring the sagging length of a new gas diffusion layer and comparing the measured sagging length with the sagging length limit value to determine the new gas diffusion layer as a normal product if the sagging length of the new gas diffusion layer is within the sagging length limit value or to determine the new gas diffusion layer as an abnormal product if the sagging length of the new gas diffusion layer exceeds the sagging length limit value.

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Figure 3:
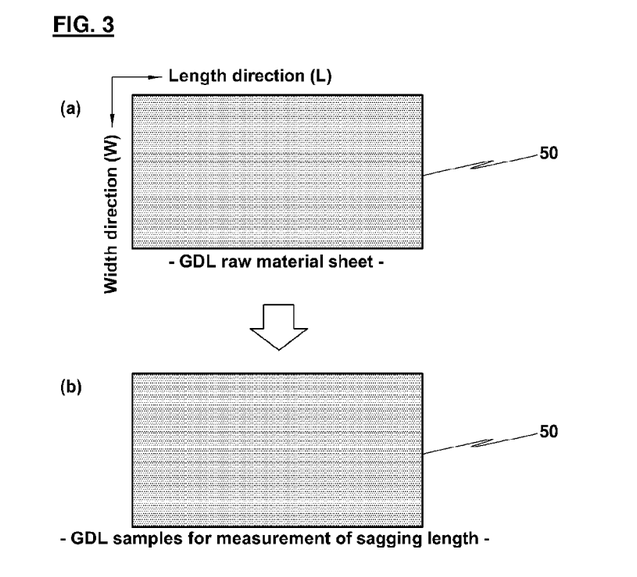
FIGS. 3A and 3B are schematic diagrams illustrating a sampling method for non-destructive and indirect measurement of bending stiffness of a GDL in accordance with the present invention.

In certain exemplary embodiments of the present invention, for example as shown in FIG. 3, FIGS. 3A and 3B are schematic diagrams illustrating a sampling method for non-destructive and indirect measurement of bending stiffness of a GDL, in which a GDL sample as a raw material sheet 50 of FIG. 3A is used as a sample for measurement of a sagging length of FIG. 3B.

As described herein, while the GDL raw material sheet is cut into samples in the conventional method, the present invention preferably uses the GDL sample 50 as a sample for indirect measurement of the bending stiffness of the GDL to suitably measure the sagging length of the GDL.

Figure 4:
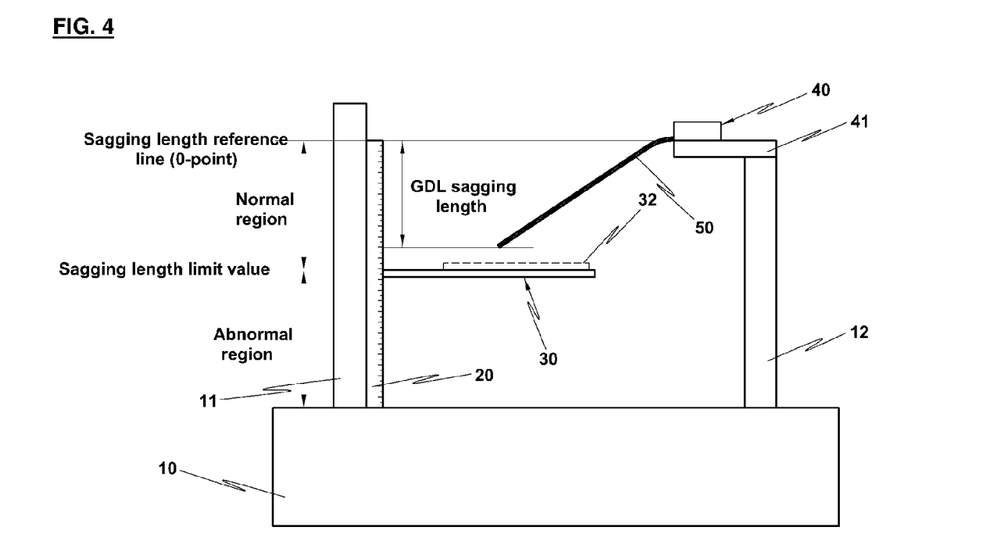
FIG. 4 is a schematic diagram illustrating an apparatus for measuring a sagging length of a GDL sample as a raw material sheet for non-destructive and indirect measurement of bending stiffness of a GDL in accordance with the present invention.

According to preferred embodiments of the present invention, and as shown in FIG. 4, for example, FIG. 4 is a schematic diagram illustrating an apparatus for measuring a sagging length of a GDL sample as a raw material sheet for non-destructive and indirect measurement of bending stiffness of a GDL in accordance with the present invention.

As shown in FIG. 4, the apparatus for non-destructive and indirect measurement of the bending stiffness of the GDL in accordance with preferred embodiments of the present invention preferably includes a lower plate support 10 having a predetermined area, first and second columns 11 and 12 erected vertically on both top sides of the lower plate support 10, a sagging length measuring means 20 integrally attached to the first column 11 along the longitudinal direction to measure the sagging length of the GDL, a sagging length limit value sensor 30, in which an inner end is suitably mounted in a predetermined position of the sagging length measuring means 20 to be moved up and down and an outer end is horizontally arranged as a free end, and a GDL sample holder 40 suitably disposed on a sample support 41 mounted at the top of the second column 12 to hold a GDL sample.

Preferably, in further embodiments of the present invention, the lower plate support 10 is suitably provided merely as a support means for supporting the first and second columns 11 and 12 and may be a single lower plate support 10 for suitably supporting the first and second columns 11 and 12 at the same time or a plurality of lower plate supports 10 for supporting the first and second columns 11 and 12 individually. Moreover, in other further preferred embodiments of the present invention, the first and second columns 11 and 12 can be suitably installed vertically on the floor of the place where the apparatus is to be installed without the use of the lower plate support 10.

In other further embodiments of the present invention, the sagging length measuring means 20 may preferably include a sagging length measuring ruler with gradations suitably marked on a body to allow a user to determine the sagging length of a GDL sample with the naked eye or a laser optical sensor.

For example, in other embodiments of the present invention, a laser optical sensor mounted in the body of the sagging length measuring means 20 irradiates a laser beam to the position of the GDL sample before sagging and suitably receives the reflected beam such that a controller (not shown) performs calculation of the position of the GDL sample before sagging. Subsequently, in other further embodiments, the laser optical sensor irradiates a laser beam to the lowest position of the GDL sample after sagging and receives the reflected beam such that the controller performs calculation of the position of the GDL sample after sagging. Consequently, the controller can measure the actual sagging length of the GDL sample by subtracting the position of the GDL sample before sagging from the position of the GDL sample after sagging.

In other exemplary embodiments, in particular, the sagging length limit value sensor 30 may be a manual sensor or an automatic sensor. Preferably, in the case of the manual sensor, a long slot as the sagging length measuring means 20 is suitably formed on a measuring ruler in the longitudinal direction thereof and an inner end of the sagging length limit value sensor 30 is suitably connected to the inside of the slot to be moved up and down such that the position of the sagging length limit value sensor 30 is moved up or down to change the sagging length limit value of the GDL sample to satisfy the properties of each GDL sample. On the contrary, in other embodiments of the present invention, in the case of the automatic sensor, a contact-sensitive electronic sensor 32 is suitably provided on the top surface of the sagging length limit value sensor 30 to automatically determine whether to reach a limit value or to perform sensory test by human.

For example, in certain exemplary embodiments, in the case of the manual sensor, a fixing groove (not shown) is suitably formed in the slot (not shown) of the measuring ruler of the sagging length measuring means 20 and a projection (not shown) detachably inserted and fixed to the fixing groove is integrally formed with the inner end of the sagging length limit value sensor 30 such that the up and down positions (i.e., the sagging length limit value of a normal product to satisfy the properties of the corresponding each GDL product) of the sagging length limit value sensor 30 can be adjusted by inserting the projection into the fixing groove.

Further in other preferred embodiments of the present invention, in the case of the automatic sensor, a contact-sensitive electronic sensor 32 is further provided on the top surface of the sagging length limit value sensor 30, where the GDL sample 50 is in contact therewith, and the detection value of the electronic sensor 32 is suitably displayed on a display device (not shown) by the calculation of the controller (not shown), thereby automatically determining whether to reach a sagging length limit value of the corresponding GDL sample.

Alternatively, in the case of the automatic sensor, a laser optical sensor can be used as the sagging length measuring means. Preferably, when the light irradiated from the laser optical sensor is incident on the sagging end of the GDL sample, it may be suitably determined that the sagging length of the GDL sample reaches the limit value. In other embodiments of the present invention, when the light irradiated from the laser optical sensor is not incident on the sagging end of the GDL sample, it may be suitably determined that the sagging length of the GDL sample does not reach the limit value.

Figure 5:
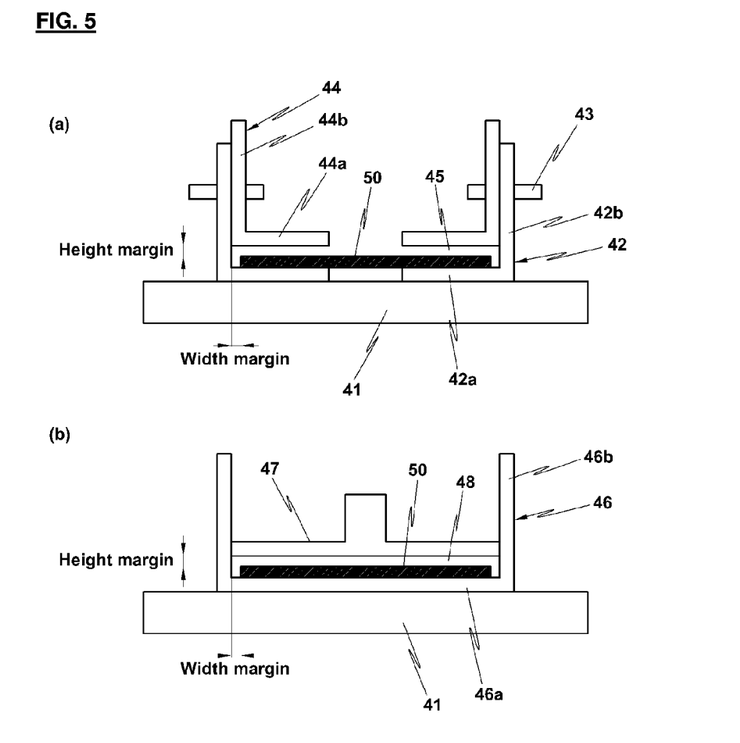
FIGS. 5A and 5B are schematic diagrams illustrating a GDL sample holder of an apparatus for non-destructive and indirect measurement of bending stiffness of a GDL in accordance with the present invention.

Meanwhile, in other preferred embodiments of the present invention, for example, as shown in FIGS. 5A and 5B, the GDL sample holder 40 may preferably have a structure in which the GDL sample 50 is directly inserted into the GDL sample holder 40, for example, as shown in FIG. 5A or a structure in which the GDL sample 50 is placed on the top of the GDL sample holder 40 and then covered with a cover as shown in FIG. 5B.

For example, in certain preferred embodiments of the present invention, for example as shown in FIG. 5A, the insertion-type structure, in which the GDL sample 50 is directly inserted into the GDL sample holder 40, preferably includes a pair of fixing plates 42 having a bent shape and integrally mounted on the sample support 41 and a pair of moving plates 44 having a bent shape, overlapping the inside of the fixing plates 42, and fixed by a position fixing pin 43, respectively. Preferably, here, a vertical plate 42b of each fixing plate 42 and a vertical plate 44b of each moving plate 44 overlap each other and are suitably connected to each other by the position fixing pin 43. Accordingly, in certain preferred embodiments, an insertion hole (not shown) that fits the fixing plate 42 and the moving plate 44 is formed such that the position fixing pin 43 is suitably inserted into the insertion hole to adjust the height of the moving plate 44 with respect to the fixing plate 42, thereby suitably fixing the position of the moving plate 44.

In particular preferred embodiments, the space between the top surface of a horizontal plate 42a of the fixing plate 42 and the bottom surface of a horizontal plate 44a of the moving plate 44 forms an insertion hole 45, into which the GDL sample 50 is suitably inserted and supported. Accordingly, the height of the insertion hole 45 is suitably maintained at an appropriate level such that one end of the GDL sample 50 is inserted into the insertion hole 45.

Accordingly, in certain preferred embodiments, the insertion hole 45 as the space between the horizontal plate 42a of the fixing plate 42 and the horizontal plate 44a of the moving plate 44 may have a height greater than the thickness of the GDL sample 50 such that the surface of the microporous layer of the GDL sample 50 is not damaged or scratched when the GDL sample 50 is suitably inserted into the insertion hole 45. Preferably, the insertion hole 45 may have a height 5% greater than the thickness of the GDL sample 50.

According to still further preferred embodiments of the present invention, the distance between the left and right vertical plates 42b of the pair of the fixing plates 42 may be 5% greater than the width of the GDL sample 50 such that the sample can be easily inserted into and removed from the insertion hole 45 before and after the measurement of the sagging length of the GDL sample 50.

In certain preferred embodiments, for example as shown in FIG. 5B, the cover-type structure preferably includes a single-type fixing plate 46 having an open top and open front and rear sides and a cover 47 suitably connected to the fixing plate 46 to be moved up and down.

For example, in certain exemplary embodiments of the present invention, a slide groove (not shown) is vertically formed on the inner surface of a vertical plate 46b of the fixing plate 46, and the cover 47 is suitably connected to the slide groove to be moved up and down. Further, a plurality of fixing grooves (not shown) are suitably formed in the slide groove of the vertical plate 46b and a projection (not shown) inserted into the fixing groove is formed such that the height of the cover 47 with respect to the fixing plate 46 can be suitably adjusted to a desired level.

Preferably, in certain preferred embodiments, the GDL sample 50 is suitably inserted into an insertion hole 48 between the top surface of a horizontal plate 46a of the fixing plate 46 and the bottom surface of the cover 47 to suitably measure the sagging length of the GDL sample 50. That is, the GDL sample 50 is preferably placed on the horizontal plate 46a of the fixing plate 46 and the cover 47 is suitably covered thereon to be fixed. Preferably, the space between the cover 47 and the GDL sample 50, i.e., the height of the insertion hole 48 may be 5% greater than the thickness of the GDL sample 50 such that the surface of the microporous layer of the GDL sample 50 is not damaged or scratched by the contact with the cover 47. Further, the distance between the left and right vertical plates 46b of the fixing plate 46 may be 5% greater than the width of the GDL sample 50 such that the sample can be easily inserted into and removed from the insertion hole 48.

In further preferred embodiments of the present invention, the GDL sample holder 40 having the above-described insertion-type or cover-type structure may be suitably formed of at least one selected from the group consisting of metal, ceramic, and polymeric materials. Preferably, the GDL sample holder 40 may be suitably formed of a lightweight and transparent material so as to minimize the damage or deformation of the GDL and allow a user to suitably observe the damage or deformation of the GDL with the naked eye during measurement of the sagging length of the GDL.

Therefore, in certain preferred embodiments of the present invention, examples of appropriate materials for the GDL sample holder 40 include, but are not limited to, acrylic polymers such as polymethylmethacrylate, polyethylmethacrylate, polymethylacrylate, polyethylacrylate, and polybutylacrylate; styrene polymers such as polystyrene, polyparamethylstyrene, and polyalphamethylstyrene; ester polymers such as polyethylene terephthalate and polybutylene terephthalate; olefin polymers such as polyethylene, ethylene vinyl acetate and polypropylene; polycarbonate polymers; polyetherimide polymers; and epoxy polymers. Further, a homopolymer of each of the above-described polymers or random, graft, block, and alternating copolymers may preferably be used solely or the polymers may be blended with at least one of thermoplastic, thermosetting, and rubber polymers or mixed with organic and inorganic materials.

Accordingly, after one end of the GDL sample 50 is suitably inserted into the GDL sample holder 40, the sagging length that the other end of the GDL sample 50 sags is suitably measured. Accordingly, by this measurement method, the sagging lengths of a plurality of GDL samples are repeatedly measured, and their average value and standard deviation are suitably obtained and compared with taber bending stiffness values which are previously measured, to establish a correlation between them, thus determining an appropriate range of sagging lengths and sagging length limit values of the GDL normal products.

Here, while the sagging length is measured after inserting the GDL sample as a raw material sheet into the GDL sample holder 40, it is possible to measure the sagging length of the GDL samples obtained by cutting the conventional GDL raw material sheet.

Accordingly, in the above-described manner, an appropriate range of sagging lengths and sagging length limit values of the GDL sample 50 are preferably used as the references for the sagging length to indirectly evaluate the bending stiffness of the GDL sample and, at the same time, the height of the sagging length limit value sensor 30 is adjusted to fit the sagging length limit value with respect to the GDL normal product 50.

Therefore, in a state where the other end of the GDL sample 50 sags and does not reach the sagging length limit value sensor 30 or does not sag below the sagging length limit value sensor 30, the gradation on the measuring ruler of the sagging length measuring means 20 is suitably read or an automatic measurement is suitably performed by the laser optical sensor. Then, preferably, if the measurement value is within the limit value, the GDL sample 50 is suitably determined as normal and is then reused, whereas, if it exceeds limit value, it is determined as abnormal and is then discarded.

Figure 6:
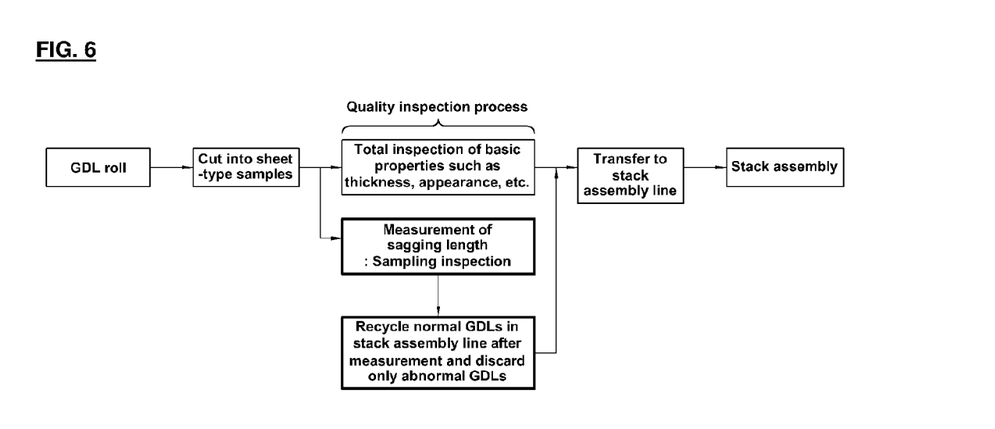
FIG. 6 is a process diagram illustrating a process of inputting a GDL sample as a raw material sheet to a process of manufacturing a fuel cell stack in accordance with the present invention.

According to certain exemplary embodiments of the present invention, for example as shown in the process diagram of FIG. 6, differently from the conventional method for measurement of bending stiffness of the gas diffusion layer, the present invention indirectly measures the bending stiffness of the gas diffusion layer through the measurement of the sagging length without damage or destruction to the GDL sample 50. Therefore, according to the present invention, it takes only about 30 seconds to select a GDL sample and measure the sagging length of the GDL sample, and thus it is possible to suitably reduce the inspection time about 40 to 120 times compared to the conventional method. Further, differently from the conventional GDL samples, which are separately formed and discarded after measurement, the GDL sample 50 of the present invention, which is determined as normal, can be suitably recycled in the assembly of the fuel cell stack.

Here, the method of determining the appropriate range of sagging lengths and the sagging length limit values of the GDL normal products by repeatedly measuring the sagging length of the plurality of GDL samples, obtaining their average value and standard deviation, comparing them with Taber bending stiffness values which are previously measured, and establishing the correlation between them are described.

In a first exemplary embodiment, five types of commercially available gas diffusion layers were selected and evaluated. In detail, three carbon fiber felt type GDLs (GDL1-F, GDL2-F, and GDL3-F) and two carbon fiber paper type GDLs (GDL4-P and GDL5-P), which were most widely used in the manufacturing of vehicle fuel cells due to their excellent properties such as reactant gas supply properties, product water discharge properties, compression properties, and handling properties, were selected and used as samples.

Moreover, although the GDL samples used in the measurement according to the present invention may comprise both a microporous layer and a macroporous substrate or only a macroporous substrate, the GDL samples comprising both the microporous layer and the macroporous substrate were used in this particular embodiment.

The microporous layer and the macroporous substrate of each of the five types of GDLs selected in this embodiment were subjected to hydrophobic treatment using a hydrophobic material, and their basic properties are shown in the following Table 1. Average values and standard deviations were suitably obtained by measuring the thicknesses of the GDL samples using a Mitutoyo thickness gauge (Mitutoyo Co., Japan) more than 50 times with respect to each of the GDL samples.

TABLE 1

| GDL code | Macroporous substrate | Microporous layer | Thickness (μm) | Weight per unit area (g/m$^2$) |
|---|---|---|---|---|
| GDL1-F | Carbon fiber felt | Included | 432 ± 5 | 140 ± 2 |
| GDL2-F | Carbon fiber felt | Included | 423 ± 5 | 149 ± 1 |

TABLE 1-continued

| GDL code | Macroporous substrate | Microporous layer | Thickness (μm) | Weight per unit area (g/m²) |
|---|---|---|---|---|
| GDL3-F | Carbon fiber felt | Included | 260 ± 6 | 110 ± 1 |
| GDL4-P | Carbon fiber paper | Included | 365 ± 6 | 100 ± 1 |
| GDL5-P | Carbon fiber paper | Included | 244 ± 3 | 87 ± 2 |

Figure 7:
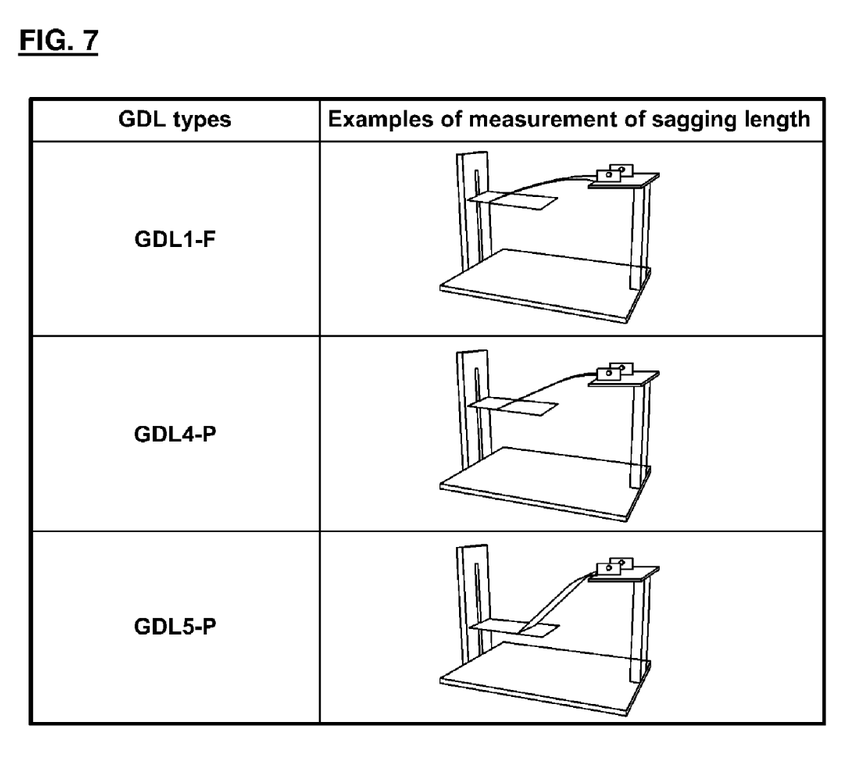
FIG. 7 shows measurements of sagging lengths of GDL samples using an apparatus for non-destructive and indirect measurement of bending stiffness of a GDL in accordance with the present invention.

When the sagging lengths of the five type of GDL samples having the properties shown in Table 1 were suitably measured using the sagging length measuring means of the present invention, it could be seen that the GDL samples had different sagging lengths according to the type and properties of the GDL samples as shown in the actual measurements of FIG. 7 (in which the measured sagging lengths of GDL1-F, GDL4-P, AND GDL5-P are shown).

Accordingly, it is possible to select appropriate GDL samples by collectively considering the properties of each given fuel cell system, operational conditions, and cell assembly conditions, obtain the average values and standard deviations of the sagging lengths of the GDL samples, and use them as a factor in suitably assessing the quality of the GDL samples.

In other exemplary embodiments of the present invention, the actual bending stiffness in the length direction of at least three samples of each type of GDL was measured by the conventional Taber method using a general Taber bending stiffness tester (Model: 150E V-5, Taber Industries, USA) at a bending angle of 15°, and the results were compared with the sagging lengths measured by the method of the present invention, which are shown in the following Table 2 and in the accompanying FIG. 8.

TABLE 2

| GDL code | Taber bending stiffness (Taber stiffness unit, $g_f \times$ cm) | Sagging length (mm) |
|---|---|---|
| GDL1-F | 75.5 ± 6.6 | 85 ± 16 |
| GDL2-F | 66.4 ± 9.1 | 95 ± 10 |
| GDL3-F | 19.4 ± 1.3 | 163 ± 7 |
| GDL4-P | 31.0 ± 0.9 | 112 ± 14 |
| GDL5-P | 6.0 ± 0.4 | 195 ± 14 |

Figure 8:
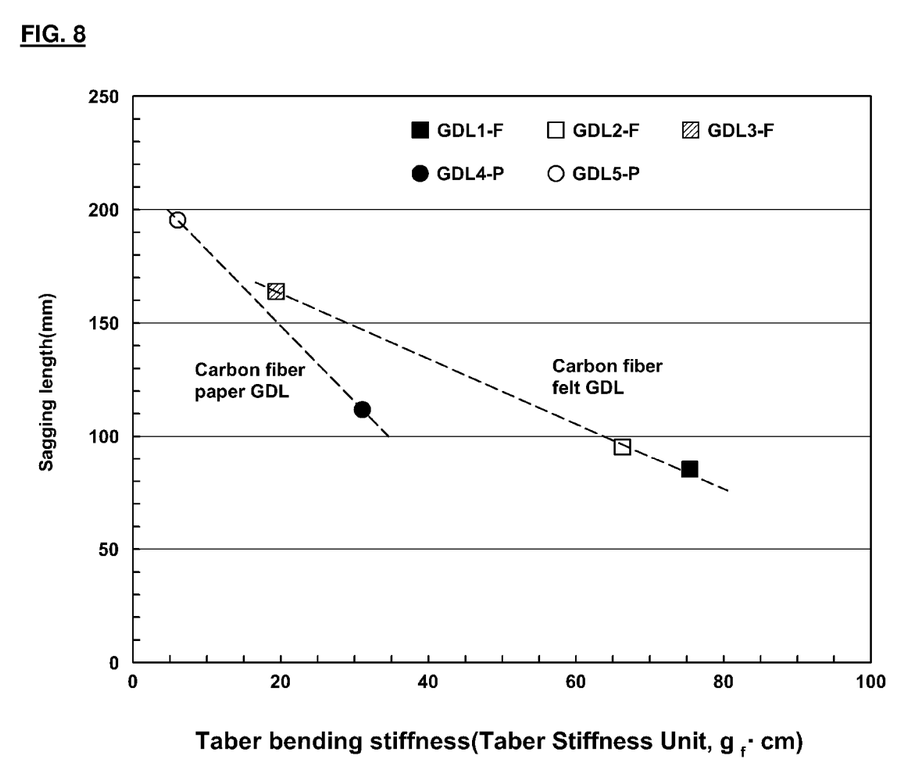
FIG. 8 is a graph showing the correlation between the sagging lengths of GDL samples measured by the present invention and the pre-measured bending stiffness of GDLs.

As shown in Table 2 and FIG. 8, the actual bending stiffness of GDL1-F was 75.5±6.6 $g_f \times$ cm and the sagging length was 85±16 mm, the actual bending stiffness of GDL2-F was 66.4±9.1 $g_f \times$ cm and the sagging length was 95±10 mm, and the actual bending stiffness of GDL3-F was 19.4±1.3 $g_f \times$ cm and the sagging length was 163±7 mm. Accordingly, it can be seen that the actual bending stiffness and the sagging length of each GDL have a correlation between them.

Therefore, the sagging length limit value with respect to the sagging length of each GDL sample is suitably defined by comparing the Taber bending stiffness values, which are previously measured. For example, in the case of the GDL1-F having the actual bending stiffness of 75.5±6.6 $g_f \times$ cm, the sagging length limit value is determined to be less than 85±16 mm. Therefore, if the sagging length of GDL1-F determined using the above-described sagging length measuring means is determined to be less than 85±16 mm, it is suitably determined as normal, whereas, if it exceeds 85±16 mm, it is suitably determined as abnormal.

As such, all of the carbon fiber felt type GDL and the carbon fiber paper type GDL have a correlation between the Taber bending stiffness and the sagging length, and thus it is possible to rapidly evaluate the bending stiffness by measuring the sagging length of the GDL using the sagging length measuring means of the present invention. Moreover, as the GDL sample used in the measurement is not damaged, it can be recycled in the assembly of the fuel cell stack. Furthermore, it takes only about 30 seconds to select a GDL sample and measure the sagging length of the GDL sample, and thus it is possible to suitably reduce the inspection time about 40 to 120 times compared to the conventional method.

As described herein, the present invention provides the following effects.

According to the present invention, and different from the conventional method for measuring the bending stiffness of a GDL sample obtained by cutting a GDL raw material sheet, it is possible to indirectly evaluate the bending stiffness of the GDL by measuring the sagging length of the GDL sample, which can be actually used for a fuel cell, without damaging or destroying the GDL sample, and thus the GDL sample used in the measurement can be recycled in the assembly of a fuel cell stack.

Further, according to the present invention, as the GDL sample prepared for the manufacturing of the fuel cell stack is used as it is for the measurement, it takes only about 30 seconds to select a GDL sample and measure the sagging length of the GDL sample, and thus it is possible to reduce the inspection time about 40 to 120 times compared to the conventional method. Accordingly, it is possible to indirectly evaluate the bending stiffness of all the gas diffusion layers, not a part of the GDL raw material sheet for the manufacturing of the fuel cell stack, and thus it is possible to considerably improve the manufacturing efficiency of the fuel cell stack.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. An apparatus for non-destructive measurement of bending stiffness of a gas diffusion layer for a fuel cell, the apparatus comprising:
   first and second columns erected vertically on a support means having a predetermined area;
   a sagging length measuring means integrally attached to the first column along the longitudinal direction to measure a sagging length of a gas diffusion layer sample;
   a sagging length limit value sensor mounted on the sagging length measuring means to determine whether the measured sagging length reaches a limit value; and
   a gas diffusion layer sample holder mounted at the top of the second column to accommodate one end of the gas diffusion layer sample having a size equal to that of a gas diffusion layer raw material sheet.

2. The apparatus of claim 1, wherein the sagging length limit value sensor has a plate-type structure and further comprises a contact-sensitive electronic sensor installed on the top surface thereof.

3. The apparatus of claim 1, wherein the gas diffusion layer sample holder comprises:
   a sample support mounted at the top of the second column;
   a pair of fixing plates integrally mounted at the top of the sample support; and
   a moving plate mounted on the inner side of each of the fixing plates to be moved up and down and fixed by a position fixing pin in a desired position,
   wherein the space between the top surface of a horizontal plate of each fixing plate and the bottom surface of a horizontal plate of each moving plate forms an insertion hole into which the gas diffusion layer sample is inserted and supported.

4. The apparatus of claim 3, wherein the height of the insertion hole is 1 to 5% greater than the thickness of the gas diffusion layer sample, and the width of the insertion hole is 1 to 5% greater than the width of the gas diffusion layer sample.

5. The apparatus of claim 3, wherein the gas diffusion layer sample holder is formed of a transparent material to allow a user to observe damage or deformation of the gas diffusion layer sample with the naked eye during measurement of the sagging length of the gas diffusion layer sample.

6. The apparatus of claim 1, wherein the gas diffusion layer sample holder comprises:
   a single-type fixing plate having an open top and open front and rear sides; and
   a cover slidably connected to a vertical plate of the fixing plate to be moved up and down,
   wherein the space between the top surface of a horizontal plate of the fixing plate and the bottom surface of the cover forms an insertion hole into which the gas diffusion layer sample is inserted and supported.

7. The apparatus of claim 1, wherein the sagging length measuring means comprises a sagging length measuring ruler having marked gradations to allow a user to determine the sagging length of the gas diffusion layer sample with the naked eye or a laser optical sensor for calculating a sagging length of the gas diffusion layer sample by detecting the lengths of the gas diffusion layer sample before and after sagging.

8. A method for non-destructive measurement of bending stiffness of a gas diffusion layer for a fuel cell, the method comprising:
   pre-measuring bending stiffness of various types of gas diffusion layers, which are to be actually assembled into a fuel cell stack;
   inserting one end of each of the gas diffusion layers into a gas diffusion layer sample holder in a non-contact manner, measuring the length that the other end of each of the gas diffusion layers sags, and obtaining an average value and standard deviation from the measured sagging lengths;
   comparing the pre-measured bending stiffness of the gas diffusion layer with the sagging length of the gas diffusion layer obtained in a non-contact manner to establish a correlation between the bending stiffness and the sagging length and, and the same time, defining the sagging length, which is correlated with the bending stiffness, as a sagging length limit value to determine a normal product; and
   measuring the sagging length of a new gas diffusion layer and comparing the measured sagging length with the sagging length limit value to determine the new gas diffusion layer as a normal product if the sagging length of the new gas diffusion layer is within the sagging length limit value or to determine the new gas diffusion layer as an abnormal product if the sagging length of the new gas diffusion layer exceeds the sagging length limit value.

9. The method of claim 8, further comprising reusing the gas diffusion layer, which is determined as a normal product, by supplying the gas diffusion layer to an actual assembly line of a fuel cell stack.

10. An apparatus for non-destructive measurement of bending stiffness of a gas diffusion layer for a fuel cell, the apparatus comprising:
    a first column and a second column, wherein the first and second columns are erected on a support means;
    a sagging length measuring means to measure a sagging length of a gas diffusion layer sample;
    a sagging length limit value sensor to determine whether the measured sagging length reaches a limit value; and
    a gas diffusion layer sample holder.

11. The apparatus of claim 10, wherein the first and second columns are erected vertically on a support means having a predetermined area.

12. The apparatus of claim 10, wherein the sagging length measuring means is integrally attached to the first column along the longitudinal direction to measure a sagging length of a gas diffusion layer sample.

13. The apparatus of claim 10, wherein the sagging length limit value sensor is mounted on the sagging length measuring means to determine whether the measured sagging length reaches a limit value.

14. The apparatus of claim 10, wherein the gas diffusion layer sample holder is mounted at the top of the second column to accommodate one end of the gas diffusion layer sample having a size equal to that of a gas diffusion layer raw material sheet.

* * * * *